(12) United States Patent
Atala et al.

(10) Patent No.: US 6,547,719 B1
(45) Date of Patent: Apr. 15, 2003

(54) PENILE RECONSTRUCTION

(75) Inventors: Anthony Atala, Weston; James J. Yoo, Brookline, both of MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/601,257

(22) PCT Filed: Oct. 30, 1998

(86) PCT No.: PCT/US98/22963
§ 371 (c)(1),
(2), (4) Date: Jul. 31, 2000

(87) PCT Pub. No.: WO99/22677
PCT Pub. Date: May 14, 1999

Related U.S. Application Data

(60) Provisional application No. 60/063,839, filed on Oct. 31, 1997.

(51) Int. Cl.[7] ................................................. A61F 5/00
(52) U.S. Cl. ..................... 600/40; 623/23.65; 623/23.71
(58) Field of Search ........................ 600/40; 623/11.11, 623/13.11, 13.17, 13.18, 23.64, 23.65, 23.66, 23.71, 23.72, 23.75, 23.76

(56) References Cited

U.S. PATENT DOCUMENTS

| | | | |
|---|---|---|---|
| 4,458,678 A | 7/1984 | Yannas et al. | 128/155 |
| 4,520,821 A | 6/1985 | Schmidt et al. | 128/334 R |
| 4,963,489 A | 10/1990 | Naughton et al. | 435/240.1 |
| 5,032,508 A | 7/1991 | Naughton et al. | 435/32 |
| 5,160,490 A | 11/1992 | Naughton et al. | 435/284 |
| 5,429,938 A | 7/1995 | Humes | 435/240.2 |
| 5,443,950 A | 8/1995 | Naughton et al. | 435/1 |
| 5,514,378 A | 5/1996 | Mikos et al. | 424/425 |
| 5,516,680 A | 5/1996 | Naughton et al. | 435/240.243 |
| 5,549,674 A | 8/1996 | Humes et al. | 623/11 |
| 5,567,612 A | 10/1996 | Vacanti et al. | 435/240.23 |
| 5,654,273 A | 8/1997 | Gallo et al. | 514/12 |
| 5,851,833 A | 12/1998 | Atala | 435/378 |

FOREIGN PATENT DOCUMENTS

| | | | | |
|---|---|---|---|---|
| WO | WO 89/01967 | | 3/1989 | C12N/5/00 |
| WO | 90/12603 | * | 11/1990 | |
| WO | 94/25079 | * | 11/1994 | |
| WO | 96/18424 | * | 6/1996 | |
| WO | WO 99/22781 | | 5/1999 | A61L/27/00 |

OTHER PUBLICATIONS

Atala, A., et al., "Formation of Urothelial Structures in Vivo from Dissociated Cells Attached to BioDegradable Polymer Scaffolds in Vitro," *J. Urol.*, vol. 148: 658–662 (Aug. 1992).

Atala, A., et al., "Implantation in Vivo and Retrieval of Artificial Structures Consisting of Rabbit and Human Urothelium and Human Bladder Muscle," *J. Urol.*, vol. 150: 608–612 (Aug. 1993).

Cilentro, B., et al., "Phenotypic and Cytogenetic Characterization of Human Bladder Urothelia Expanded in Vitro," *J. Urol.*, vol. 152: 665–670 (Aug. 1994).

Kirker–Head, C., "Recombinant Bone Morphogenetic Proteins: Novel Substances for Enhancing Bone Healing," *Vet. Surg.*, vol. 24: 408–419 (1995).

Laurencin., C., "A Highly Porous 3–Dimensional Polyphosphazene Polymer Matrix for Skeletal Tissue Regeneration," *J. Biomed. Mater. Res.*, vol. 30: 133–138 (1996).

Zdrahala, R., "Small Caliber Vascular Grafts. Part I: State of the Art," *J. Biomater. App.*, vol. 10: 309–329 (Apr. 1996).

* cited by examiner

*Primary Examiner*—John P. Lacyk
(74) *Attorney, Agent, or Firm*—Thomas J. Engellenner; Jasbir Sagoo; Nutter McClennen & Fish LLP

(57) ABSTRACT

A cartilaginous structural member (CSM) for use in penile reconstruction, for the correction of developmental defects, postoperative reconstruction, and for reconstructive preprosthetic surgery. The cartilaginous structural member (CSM) comprise of live cells seeded onto pre-formed shaped structure which may be biodegradable. The live cells may comprise chondrocyte and the cartilaginous structural member (CSM) for use in reconstructive surgery may be constructed of polyglycolic acid. The implant structure is applicable to use for the regeneration and reconstruction or augmentation of semirigid members of the body such as the penis, nose, ear and locations which naturally has cartilage. Further, the cartilaginous structural member (CSM) may be used in plastic surgery such as, for example, breast augmentation or pectoral augmentation. The cartilaginous structural member (CSM) may be a composite cartilaginous structural member (CSM) comprising additional anchoring and strengthening elements for anchoring or changing the structural strength of said composite cartilaginous structural member (CSM).

31 Claims, 12 Drawing Sheets

RETRIEVAL
1, 2, 4, 6 MONTHS

Ramp Compression
Speed: 200 um/s

Ramp Tension with Release
Speed: 200 um/s

Cyclic compression
speed: 500 um/s
Data cycle: 5

Cyclic Compression
Speed: 20000/s
Distance: 5000 um
Data Cycle: 5

PENILE RECONSTRUCTION

The application claims the benefit of provisional application 60/063,839 filed Oct. 31, 1997.

BACKGROUND OF THE INVENTION

1. Field of the Invention

The invention is directed to methods and materials useful in treating anatomical defects by employing tissue engineered structural support members and in particular to methods and materials useful in penile reconstruction.

2. Description of the Background

Conditions such as inadequate and ambiguous genitalia, caused by aphallia, rudimentary penis, severe hypospadias, traumatic injury or pseudohermaphroditism, require surgical intervention. Sex assignment in these patients is made after a thorough diagnostic evaluation and careful consultation with the family. The decision is made based on external genital morphology, hormonal sex and the established gender role. In numerous instances, a decision is made to rear the child as a female, regardless of the karyotype, due to surgical difficulties and poor results with phallic construction.

The penis consists of two parallel cylindrical bodies, the corpora cavemosa and beneath them the corpus spongiosum, through which the urethra passes. The urethra runs along the underside of the penis then rises to open at the expanded, cone-shaped tip, the glans penis, which fits like a cap over the end of the penis. Loose skin encloses the penis and also forms the retractable foreskin or prepuce. The root of the penis is attached to the descending portions of the pubic bone by the crura, the latter being the extremities of the corpora cavemosa.

There are many causes of impotence. Organic impotence is the loss of the ability to obtain or maintain a functional erection due to the interruption of certain physiologic processes. Causes of organic impotence include trauma such as spinal cord injury or pelvic fracture; postoperative complications such as prostatectomy, cystectomy, external sphincterotomy and abdominal perineal resection; vascular disease such as arteriosclerosis or priapism; neurologic disease such as peripheral neuropathy and multiple sclerosis; endocrinologic and metabolic disease such as diabetes, hypogonadism and renal failure; and medication such as estrogen, parasympatholytic, morphine, and heroin. The complex reflexes entailed in the mechanism of erection are also affected by physiological factors.

Phallic construction was initially attempted in the late 30's using autogenous tissue (See e.g., Goodwin, W. E. et al., Phalloplasty. J. Urol., 68: 903, 1952). Rib cartilage had been used as a stiffener in patients with traumatic penile loss. This method involved multiple stage surgery which did not have a cosmetically satisfactory result (Frumpkin, A. P.: Am. Rev. Sov. Med., 2: 14, 1944). Silicone prostheses have become popularized in the 1970s (Bretan, P. N. Jr.: In: Genitourinary Prostheses. Montague, D. K. (ed), Philadelphia, W. B. Saunders Co., 1989; Small, M. P. et al., Urology, 5: 479, 1975). Although silicone penile prostheses are an accepted treatment modality for adults, complications such as erosion and infection remain a problem (Nukui, F. et al., Int. J. Urol., 4: 52, 1997; Kardar, A. et al., Scan. J. Urol. & Nephrol., 29: 355, 1995). Other problems reported with synthetic prostheses include extrusion through the urethra or sink of the dorsal penile shaft; lymphatic edema; irritation of the glans at the corona; slippage of the glans over the prosthesis; infection of the corpora cavernosa; crural perforation; midshaft septal perforation; and penile pain (Small, M. P. et al., Urology, 5: 479, 1975).

Although silicone penile prostheses are an accepted treatment modality for adults requiring penile reconstruction, its use has not been generally applied to the pediatric population, mainly due to the long-term problems associated with these artificial devices. Thus, there is a need for biocompatible and elastic penile implants that could be used in children who require genital reconstruction.

SUMMARY OF THE INVENTION

The present invention overcomes the problems and disadvantages associated with current strategies and designs in tissue and organ reconstruction reforming structural support members.

One embodiment of the invention is directed to an implantable structural member for use in treating a patient having an anatomical defect which is not caused by absent, damaged, or diseased cartilage. The defect is treated, at least in part, by providing structural support to adjacent tissue. The structural member is made from a polymeric matrix shaped in the form of the desired support member with dissociated cartilage-forming cells deposited on and in the matrix such that when the matrix is implanted, a cartilaginous structural member is formed. The cartilaginous structural member has controlled biomechanical properties to provide the required structural support in the area of the defect.

Another embodiment of the invention is directed to a method for treating a patient which has an anatomical defect not caused by absent, damaged or diseased cartilage. The defect is of a type that can be treated, at least in part, by providing structural support to adjacent tissue. The method involves providing a polymeric matrix shaped in the form of a desired support member. Dissociated cartilage forming cells are deposited on and in the matrix to form a matrix/cell construct. The matrix/cell construct is implanted in the patient at a site which needs structural support so that the construct forms a cartilaginous structural member with controlled biomechanical properties to provide the required structural support in the defect area.

A further embodiment of the invention is directed to a method for reconstructing the penis of a patient who needs such treatment. A biocompatible synthetic or natural polymeric matrix shaped to form a structural member and adopted to fit within the corpora cavemosa or to replace the corpora cavernosa is provided. Cartilage-forming cells is deposited on and in the polymeric matrix to form a matrix/cell construct. The matrix/cell construct is implanted into the corpora cavernosa of the patient so that a cartilaginous structural member is formed in vivo with controlled biomechanical properties thus providing the reconstructed penis with sufficient stiffness and bending strength to serve as a functional organ.

Other embodiments and advantages of the invention are set forth, in part, in the description which follows and, in part, will be obvious from this description and may be learned from the practice of the invention.

DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 6 depicts a schematic diagram of study wherein autologous chondrocytes are isolated from rabbit ears, expanded and seeded onto pre-formed polymer rods. Cell-polymer scaffolds are implanted intracorporally.

Figure 1:
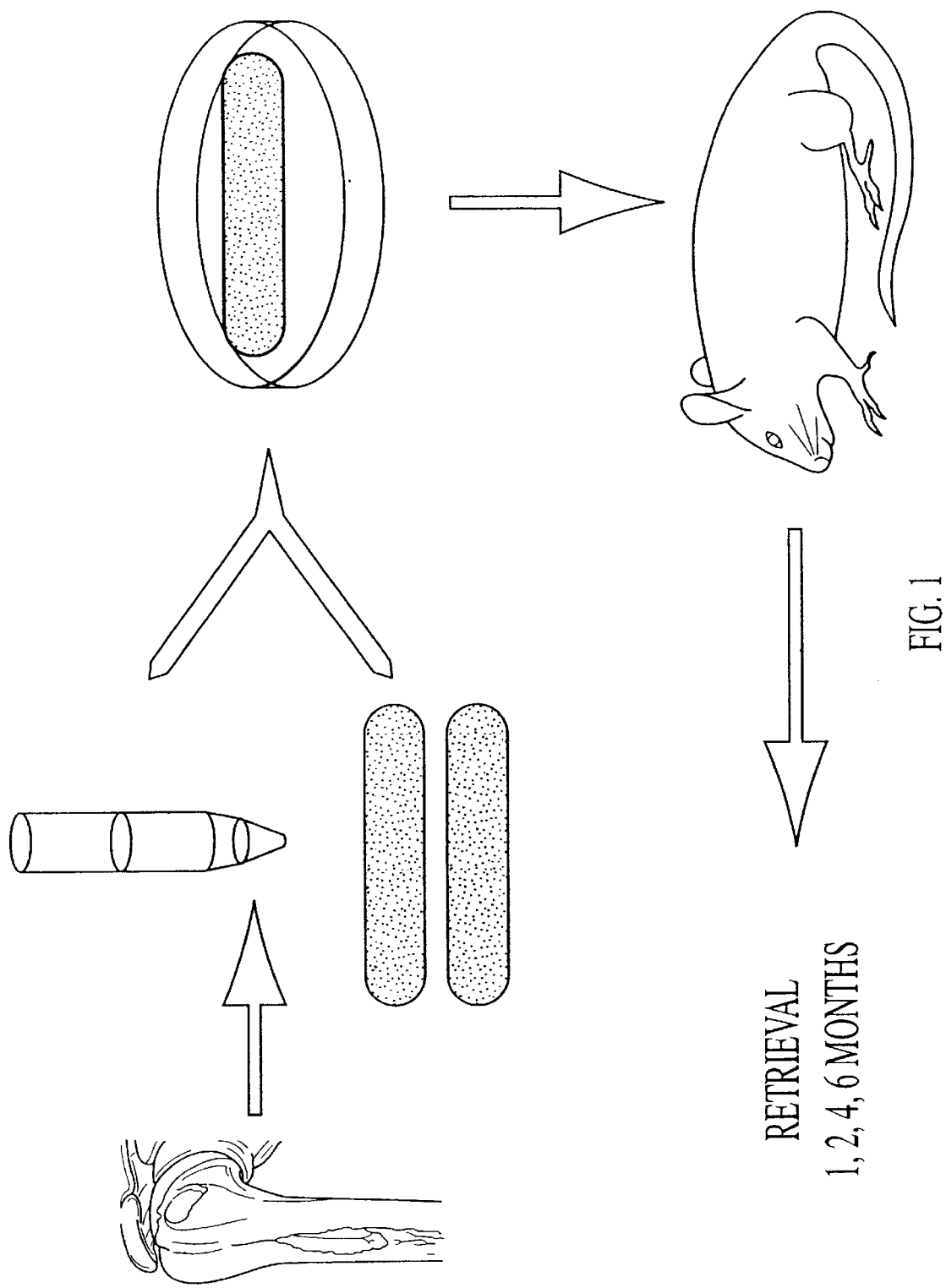
FIG. 1 depicts a schematic diagram of study.

The specimens are retrieved for analyses at 1, 2, 3 and 6 months, after implantation.

FIG. 7 panel (A) depicts a retrieved genitalia from a control rabbit at 1 month after implantation shows cartilage formation in one of the corpus cavemosa, while the control corpus cavemosum has a normal appearance; panel (B) depicts retrieved cartilage rod 1 month after implantation.

FIG. 8 depicts retrieved cartilage rod specimens at 3 months. Panel (A) depicts cartilage tissue has formed within both corpora (C). H & E, reduced from ×25. Panel (B) depicts mature chondrocytes, enclosed within lacunae, are found adjacent to, the tunica albuginea (T). H & E, reduced from ×250.

FIG. 9 depicts highly sulfated mucopolysaccharides are detected at 6 months after implantation. Panel (A) depicts toluidine blue staining, reduced from ×250. Panel (B) depicts aldehyde fuchsin-alcian blue starting, reduced from ×250.

DESCRIPTION OF THE INVENTION

In its broadest aspect the present invention relates to methods and materials for treating a patient having an anatomical defect that is not caused by absent, damaged or diseased cartilage and that can be treated, at least in part by providing structural support to tissue adjacent or comprising the defect. The requisite structural support can be provided in accordance with the present invention, by tissue engineered cartilaginous structural members of a predetermined shape and having controlled biomechanical properties. While described below primarily in connection with rod shaped members for penile reconstruction, the present invention contemplates structural members of any configuration and cross section for use in any part of the body where structural support will correct or aid in the correction of noncartilage structural defects.

The invention is directed to the use of a cartilaginous structural member to provide structural reinforcement to a region of a patient. Surgical procedures and injuries often result in a weakened body structure in a patient. For example, the removal of a diseased or injured organ such as a lung or kidney results in a large cavity in a patient. A cartilaginous structural member (CSM) can provide structural support in the cavity left behind after removal of such organs. One advantage of the CSM it that it is made of a material which is suitably soft to allow a surgeon to rapidly shape and model it during implantation. Further, because of the ability to manufacturer CSM in vitro, a plurality of CSM structures can be prefabricated before an operation. The surgeon is thus able to select the most suitable CSM structure in terms of size and structural properties during an operation. Structural properties that can be selected for include structural strength, resistance to bending, twisting and the like.

Another embodiment of the invention is directed to a CSM which can be fabricated with variable structural strength to allow the structure to be specifically tailored for individual applications. The CSM is capable of providing a variable degree of structural support depending on the specific need of the location and the patient. For example, CSM structures can be manufactured in sheets, columns, fluted columns, polygons, spheres or any complex shape suited to provide structural support in a body cavity. Alternatively, the CSM can be manufactured in a solid block and shaped before or after seeding by chondrocytes. The shape of the CSM can be determined, for example, by CAT scan or MRI imaging of a patient before surgery. Fabrication can be by hand or by computer aided design-computer aided manufacturing (CAD-CAM) systems.

Cells

Cartilage forming cells may be isolated according to procedure described in issued U.S. Pat. No. 5,041,138 which is herein specifically incorporated by reference. Briefly, articulating cartilage was obtained from the shoulders of calves under two weeks of age. The shoulders were washed in Povidone-Iodine 10% and the cartilage from the articulating surfaces of the joint were isolated and cut into pieces with dimensions of less than 5 mm per side. Then the cartilage is washed twice in Phosphate Buffered Saline (PBS) with electrolytes and adjusted to neutral pH and incubated at 37° C. in a solution of 0.2% clostridial collagenase (Worthington CLS II, 140 U/mg) and agitated overnight as described by Klagsbrun, (Methods in Enzymology, 58: 560, 1979). This suspension was then filtered using a 153 mg nylon sieve (Tetko, Elmford, N.Y. 10523). The cells were then removed from suspension using centrifugation, washed twice with PBS solution and counted with a hemocytometer. The solution was centrifuged at 1800 rpm and the supernatant above the cell suspension was removed via suction using a micro pipette until the volume of the solution yielded a chondrocyte concentration of 50 million cells per milliliter.

Cells can be isolated from any tissue that comprise chondrocytes. Tissues which can serve as a source for chondrocytes include, for example, cartilage from ribs, nose, ear, joints, unerupted tooth, hyaline cartilage, elastic cartilage and fibrocartilage. Because of the ability to expand an initial chondrocyte population, only a small sample of tissue is required. The tissue can be easily and quickly collected using a biopsy gun with a local anesthetic.

Chondrocytes (such as autologous chondrocytes) can be cultured in vitro, if desired, to increase the number of chondrocytes available for seeding on the polymeric matrix "scaffold." The use of allogenic cells, and more preferably autologous chondrocytes, is preferred to prevent tissue rejection. However, if an immunological response does occur in the subject after implantation of the CSM, the subject may be treated with immunosuppressive agents such as, for example, cyclosporin or FKSO6, to reduce the likelihood of rejection of the CSM. In certain embodiments, chimeric cells, or cells from a transgenic animal, can be seeded onto the polymeric matrix.

Cells may be transfected prior to seeding with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection can also be used for gene delivery. Chondrocytes can be transfected with specific genes prior to polymer seeding. The cell-polymer construct can carry genetic information required for the long-term survival of the host or the tissue engineered neo-organ. For example, cells may be transfected to express insulin for the treatment of diabetes.

Chondrocyte cultures may be prepared with or without a cell fractionation step. Chondrocyte fractionation may be performed using techniques, such as florescent activated cell sorting, which is known to those of skill in the art. Cell fractionation may be performed based on cell size, DNA content, cell surface antigens, and viability. For example, chondrocytes may be enriched and contaminating cells such as fibroblasts may be reduced. While cell fractionation may be used, it is not necessary for the practice of the invention.

Cell fractionation may be desirable, for example, when the donor has diseases such as cancer or metastasis of other tumors to the cartilage. A chondrocyte population may be sorted to separate malignant tumor cells from normal noncancerous chondrocytes. The normal noncancerous chondrocytes, isolated from one or more sorting techniques, may then be used for CSM. After the patient is treated for cancer the CSM may be used for penile reconstruction.

Another optional procedure in the method is cryopreservation. Cryogenic preservation may be useful, for example, to reduce the need for multiple invasive surgical procedures. Chondrocyte may be amplified and a portion of the amplified cells may be used and another portion may be cryogenically preserved. The ability to amplify and preserve cells allows considerable flexibility in the choice of donor cells. For example, cells from a histocompatible donor, may be amplified and used in more than one recipient.

Another example of the utility of cryogenic preservation is in tissue banks. Donor cells may be cryopreserved along with histocompatibility data. Donor cells may be stored, for example, in a donor tissue bank. As tissue is needed for CSM, cells may be selected which are most histocompatible to the patient. Patients who have a disease or undergoing treatment which may require CSM may cryogenically preserve a population of chondrocyte. Later, if needed, the cryogenically preserved chondrocytes may be thawed and used for treatment. For example, if cancer reappeared after penile reconstruction, cryogenically preserved cells may be used for penile reconstruction without the need isolate more tissue from the patient for culture.

Polymeric Matrix Material

Biocompatible material and especially biodegradable material is the preferred material for the construction of the polymeric matrix. Biocompatible refers to materials that do not have toxic or injurious effects on biological functions. Biodegradable refers to material that can be absorbed or degraded in a patient's body. Examples of biodegradable materials include, for example, absorbable sutures. Representative materials for forming the biodegradable structure include natural or synthetic polymers, such as, for example, collagen, poly(alpha esters) such as poly(lactate acid), poly (glycolic acid), polyorthoesters amd polyanhydrides and their copolymers, which degraded by hydrolysis at a controlled rate and are reabsorbed. These materials provide the maximum control of degradability, manageability, size and configuration. Preferred biodegradable polymer materials include polyglycolic acid and polyglactin, developed as absorbable synthetic suture material. Polyglycolic acid and polyglactin fibers may be used as supplied by the manufacturer. Other biodegradable materials include cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

In some embodiments, attachment of the cells to the polymer is enhanced by coating the polymers with compounds such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. Mechanical and biochemical parameters ensure the polymer provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix. Similarly, polymers containing peptides such as the attachment peptide RGD (Arg-Gly-Asp) can be synthesized for use in forming matrices.

A presently preferred biocompatible polymer is Polyglactin and polyglycolic acid. Polyglactin was developed as absorbable synthetic suture material, a 90:10 copolymer of glycolide and lactide, manufactured as Vicryl braided absorbable sutures (Ethicon Co., Somerville, N.J.) (Craig P. H., Williams J. A., Davis K. W., et al.: A Biological Comparison of Polyglactin 910 and Polyglycolic Acid Synthetic Absorbable Sutures. Surg. 141; 1010, (1975)). Polyglactin and polyglycolic acid fibers can be used as supplied by the manufacturer. The biocompatible polymer may be shaped using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the matrix. Next a solvent is used to dissolve away one of the components, resulting in pore formation. (See Mikos, U.S. Pat. No. 5,514,378, hereby incorporated by reference). In nucleation, thin films in the shape of a matrix are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a matrix structure with uniform pore sizes.

Coating refers to coating or permeating a polymeric structure with a material such as, for example, liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix can be weaved, compression molded and glued together. Furthermore different polymeric materials shaped by different processes may be joined together to form a composite shape. The composite shape can be a laminar structure. For example, a polymeric matrix may be attached to one or more polymeric matrixes to form a multilayer polymeric matrix structure. The attachment may be performed by any suitable means such as gluing with a liquid polymer, stapling, suturing, or a combination of these methods. In addition, the polymeric matrix may be formed as a solid block and shaped by laser or other standard machining techniques to its desired final form. Laser shaping refers to the process of removing materials using a laser.

The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies. In vitro cell attachment and viability can be assessed using scanning electron microscopy, histology, and quantitative assessment with radioisotopes.

In one preferred embodiment, the polymeric matrix is formed with a polyglycolic acid with an average density of about 58 milligrams per cubic centimeter. The unwoven mesh may compose fibers with a diameter of 15 $\mu$m and greater than 95% porous before seeding. In a preferred embodiment, the polymer scaffolds are designed to degrade via hydrolysis over about 6 to about 8 weeks. The polymeric matrix may be sterilized in ethylene oxide and kept under sterile conditions until use.

Polymeric matrixes can be treated with additives or drugs prior to implantation (before or after the polymeric matrix is seeded with cells), e.g., to promote the formation of new tissue after implantation. Thus, for example, growth factors, cytokines, extracellular matrix components, and other bioactive materials can be added to the polymeric matrix to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. Vet. Surg. 24 (5): 408–19 (1995)). For example, when polymeric matrixes (optionally seeded with endothelial cells) are used to augment vascular tissue, vascular endothelial growth factor (VEGF, see, e.g., U.S. Pat. No. 5,654,273 herein incorporated by reference) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the polymeric matrix, if added cells are employed. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

One preferred supporting matrix is composed of crossing filaments which can allow cell survival by diffusion of nutrients across short distances once the cell support matrix is implanted.

Polymeric Matrix Structure

The polymeric matrix may be fabricated with controlled pore structure as described above. The size of the pores may be used to determine the cell distribution. For example, the pores on the polymeric matrix may be large to enable chondrocytes to migrate to the interior of the structure.

The polymeric matrix may be shaped into any number of desirable configurations to construct a cartilaginous structural member (CSM) to satisfy any number of overall system, geometry or space restrictions. For example, in the use of the polymeric matrix for penile reconstruction, the CSM may be of an elongated cylindrical shape. Preferably of a dimension that the length is at least about 3 times the diameter. The CSM may be a solid rod or a hollow rod. The hollow rod may have a space adapted for the placement of a urethra. The urethra may be natural, synthetic, or an engineered neo-urethra. A CSM may be shaped to replace one or both corpora cavernosa. In the use of CSM in penile reconstruction, the CSM should roughly resemble the anatomical part it was meant to replace. In the cases where CSM is implanted to provide support for or to replace the corpora cavernosa, the CSM may be shaped similar to the corpora cavernosa. That is, the CSM may be shaped to form two elongated cylinders. In the case of more extensive penile reconstruction, the CSM may be shaped to resemble an elongated rod. When designed to replace both corpora cavemosa, the CSM may have the shape of an elongated cylinder with a kidney shaped cross section.

It may be desirable to have a CSM with variable structural strength. For example, it may be desirable for the structural strength of the penile implant to be strong at a point distal from the body but to be relatively weaker at a point nearer the body. In such a way, the reconstructed penis may still have sufficient structural strength for intercourse while maintaining sufficient flexibility at other times. In another embodiment, the CSM may be relatively strong at a position proximal to the body and relatively week at a position distal from the body. In addition, the CSM may be relatively strong at both ends and weak and more flexible in the middle. The compressive and bending strength of the CSM may be varied using common fabrication techniques. For example, bending strength may be increased or decreased by thickening or thinning (weakening) a solid CSM. Similarly, thickening or thinning the walls of a hollow CSM will have similar effects. Longitudinal ridges, lateral ridges, bias ridges, honeycomb and cellular structure may also be used to alter structural strength. Methods for altering the structural strength of materials by shaping are known to those with training in mechanical engineering and may be incorporated in the construction of the CSM. An optional method for the construction of the flexible polymer scaffolds is to strengthened it by coating some portion or all of the preformed polymer scaffold with an additional liquefied copolymer such as, for example, poly-DL-lactide-co-glycolide 50:50 (i.e., 50%:50%).

One important feature of a penile prosthesis is the rigidity needed to maintain its configuration. In the adult population, the prosthesis should be able to withstand certain pressure to allow coitus. The cartilage rods engineered of the invention showed adequate biomechanical parameters. The compression, tension and bending studies performed demonstrated that the cartilage rods were readily elastic and can withstand high degrees of pressure.

The polymeric matrix may be made flexible or rigid, depending on the desired final form, structure and function. An apparent advantage of using the fibrous matrices is the ease in reshaping and rearranging the structures at the time of implantation.

The polymeric matrix may be sterilized using any known method before use. The methods used depend on the material used in the polymeric matrix. Examples of sterilization methods include steam, pressurized steam, dry heat, radiation, gases such as ethylene oxide, gas and boiling.

Seeding

Braided threads of polyglactin 910, a 90–10 copolymer of glycolide and lactide, coated with polyglactin 370 and calcium stearate (vicryl suture material, Ethicon Co., Somerville, N.J.) were then cut into pieces of approximately 17 mm in length. One end was unbraided to expose multiple fibers, 14 microns in diameter. A knot was placed at the other end to aid in locating the polymer during subsequent biopsies. Two polymer fibers were placed into each of 26 Falcon tissue culture dishes, 35 mm in size. Two hundred ml of the above solution was placed on the two fibers in each of 15 wells, thus exposing 30 fibers to the solution containing chondrocytes and keeping 22 polymers free from exposure to chondrocytes to serve as controls. Next, 2 ml of a solution containing Hamm's F-12 culture media and 10% fetal calf serum with L-glutamine (292 mg/cc), penicillin (100 U/cc), streptomycin (100 mg/cc) and ascorbic acid (5 mg/cc) was added to each well. After being incubated at 37° C. for 3, 6, 11, 18, 21 and 28 days, six fibers from each group were examined grossly for the presence and morphologic appearance of chondrocytes using phase contrast microscopy and then evaluated histologically using Hematoxylin and Eosin staining and Aldehyde-Alcian Fuschin stain for chondroitin sulfate, the strongly acidic sulfate of mucopolysaccharides of the cartilage.

The seeding the polymeric matrix with cells may be performed a number of methods which is discussed in issued U.S. Pat. No. 5,041,138 which is herein specifically incorporated by reference.

Penile Reconstruction

Implantation and reconstruction may be performed using a number of techniques. Briefly, the patient is placed in the dorsal lithotomy position and a catheter is placed in the urethra for identification purposes. A vertical midline incision is made from the base of the scrotum toward the anus and the incision is carried down to the bulbocavemosus muscle. The cavemosus muscle and urethra are retracted to one side and the ischial cavernosus muscle and the crus of the penis are identified. Once the crus has been identified, it is opened for a length of about 2 centimeters. Hegar dilators are used to dilate the crus of the penis proximally to the ischial tuberosity and distally for the complete extent of the corpora cavemosa The CSM is inserted inside the corpora. The prosthesis should fit firmly against the wall of the corpora cavemosa. Ideally, a few CSM of different sizes should be provided. Alternatively, the surgeon may trim the CSM to fit the patient. After one prosthesis is inserted, the same procedure may be carried out on the contralateral side. The incisions in the corpora are then closed with a running suture of 3-0 chromic catgut. The remainder of the wound is closed in a routine manner. During the procedure, the CSM is soaked in an antibiotic solution such as, for example, polymyxin-neomycin. After the insertion, the wound is irrigated with the same solution. Broad spectrum antibiotic is given and continued postoperatively.

The CSM may also be used for total penile reconstruction. Microsurgical techniques for penile reconstruction are known (see e.g., Jordan et al., J. Urol. 152:410–414, 1994). Such techniques include the creation of a sensate neophallus initially through coaptation of the flap nerves to the genitofemoral or ilioinguinal nerves; coaptation of the local nerves of the fasciocutaneous flaps to the dorsal nerves of the penis; reconstruction using gracilis musculocutaneous flaps and ractus abdominis musculocutaneous flaps with supplementary free flaps for sensate skin coverage; faciocutaneous forearm free flap reconstruction. A neo-urethra may be fabricated along with the neophallus for a complete reconstruction. The neo-urethra may be fabricated separately and attached to the neophallus before implantation. Alternatively, the neourethra may be part of the original CSM structure which is populated with two different cell types. Thus, total phallic construction can be achieved. Small biopsy specimens can be obtained from the patient's ear and bladder. Chondrocytes and urothelial cells can be grown and expanded separately. The cells can be seeded on separate preformed biodegradable polymer scaffolds followed by a single stage operation to construct a phallus with an adequate neourethra.

CSM can replace intracorporeal implants, thus eliminating possible complications such as erosion and infection. A similar approach can be applied to patients presenting with recurrent priapisms secondary to sickle cell anemia. Currently available managements have not proven to prevent recurrent priapism. Implantation of engineered natural prostheses composed of autologous chondrocytes would permanently eliminate the problems of blood engorgement within the corpora.

Another utility for CSM is in treatment of a painful genital conditions such as the Peyronie's disease. The therapeutic approach for these instances can include using cells transfected with genetic material. The transfected cell-polymer scaffolds form an organ-like structure with functional expression of the delivered genes. Genes regulating inflammation and fibrosis can be delivered into the engineered penile prostheses composed of autologous chondrocytes. This gene modified prosthesis would carry all the genetic information required for the functional expression in order to prevent recurrent diseases.

The engineered cell-polymer scaffolds were snugly implanted within the corpus cavemosa without any technical difficulties. The polymer scaffolds used in this study were designed to degrade in 6 to 8 weeks. The seeded cells readily formed mature cartilage tissue in vivo, replacing the degrading polymer fibers during this period. The engineered cartilage remained at the site of initial implantation without any evidence of infection, inflammation or erosion. Histologically, the retrieved rods showed adequate formation of mature cartilage, as evidenced by the presence of chondrocytes within lacunae and the presence of highly sulfated mucopolysaccharides.

The use of engineered cartilage prostheses may be applicable clinically to patients undergoing penile reconstruction for either congenital or acquired conditions. This technology may also be used in adults with erectile dysfunction. The autologous cartilage tissue, made of the patient's own cells, can be placed intracorporally.

Other embodiments and advantages of the invention are set forth, in part, in the description which follows and, in part, will be obvious from this description and may be learned from practice of the invention.

EXAMPLES

Example 1

Construction of Polymeric Matrix

Unwoven sheet of polyglycolic acid felt with a density of about 58 milligrams per cubic centimeter was configured into cylindrical rods of about 1 cm in diameter and about 2 cm or 3 cm in length. The unwoven mesh was composed of fibers with a diameter of about 15 $\mu$m, interfiber distance between 0–200 microns and was greater than about 95% porous before seeding. The scaffold was designed to degrade via hydrolysis over a period of about 6 to about 8 weeks. Optionally, the flexible scaffold was coated with a liquefied copolymer (poly-DL-lactide-co-glycolide 50:50, 80 mg/ml methylene chloride) in order to achieve adequate mechanical characteristics. The polymer scaffolds were sterilized in ethylene oxide and kept under sterile condition until cell seeding.

Example 2

Cell Culturing and Seeding

Hyaline cartilage was obtained from the articular surface of calf shoulders. Chondrocytes were harvested under sterile conditions using a previously described technique (Atala, A. et al., J Urol, 150: 745–747, 1993; Atala, A., et al., J Urol, 152: 641–643, 1994; Klagsbrun, M. Methods Enzymol., 58:560, 1979). Briefly, articulating cartilage was obtained from the shoulders of calves under two weeks of age slaughtered earlier in the day. The shoulders were washed in Povidone-Iodine at a concentration of about 10% (Betadine, Purdue Frederick Co., Norwalk, Conn.) solution, then, under sterile conditions, the muscle attachments were sharply dissected from the underlying bone to expose the joint surfaces. The cartilage from the articulating surfaces of the joint were sharply dissected from the underlying bone using a #10 scalpel (Bard-Parker, Rutherford, N.J.). The cartilage was cut into pieces with dimensions of less than about 5 mm per side and washed twice in Phosphate Buffered Saline (PBS) with electrolytes and adjusted to neutral pH. The cartilage was then incubated at about 37° C. in a solution of about 0.2% clostridial collagenase (Worthington CLS II, about 140 units per milligram) and agitated overnight as described by Klagsbrun, (Methods in Enzymology, Vol. VIII). This suspension was then filtered using a 153 mg nylon sieve (Tetko, Elmford, N.Y. 10523). The cells were then removed from suspension using centrifugation, washed twice with PBS solution and counted with a hemocytometer. The solution was centrifuged at about 1800 rpm and the supernatant above the cell suspension was removed via suction using a micro pipette until the volume of the solution yielded a chondrocyte concentration of about 5 million cells per cubic centimeter. The isolated cells were grown and expanded in culture in Hamms F-12 media (Gibco, Grand Island, N.Y.) containing 10% fetal calf serum (Biowhitaker), 5 micrograms/ml ascorbic acid, 100 micrograms/ml streptomycin and 100 units/mi penicillin and grown under 5% carbon dioxide. The chondrocytes were trypsinized about 5 weeks to about 8 weeks after initial harvest and counted using a hemocytometer. The cells were seeded onto preformed cylindrical polyglycolic acid polymer rods at a concentration of about 50 million chondrocytes per cubic centimeter.

Example 3

Implantation and Analysis

A schematic of this study is shown in FIG. 1. A total of 40 polymer scaffolds were implanted in the subcutaneous space of 20 athymic mice. Each mouse had 2 implantation sites consisting of a control (polymer alone), and polymer scaffolds seeded with chondrocytes. Mice were sacrificed at 1, 2, 4 and 6 months after implantation.

Figure 2A:
FIG. 2 depicts (A) cartilage rods implanted in vivo; (B) retrieved cartilage rod showing a well formed milky white rods shaped cartilage structure; and (C) cross section of the retrieved cartilage rod.
Figure 2B:
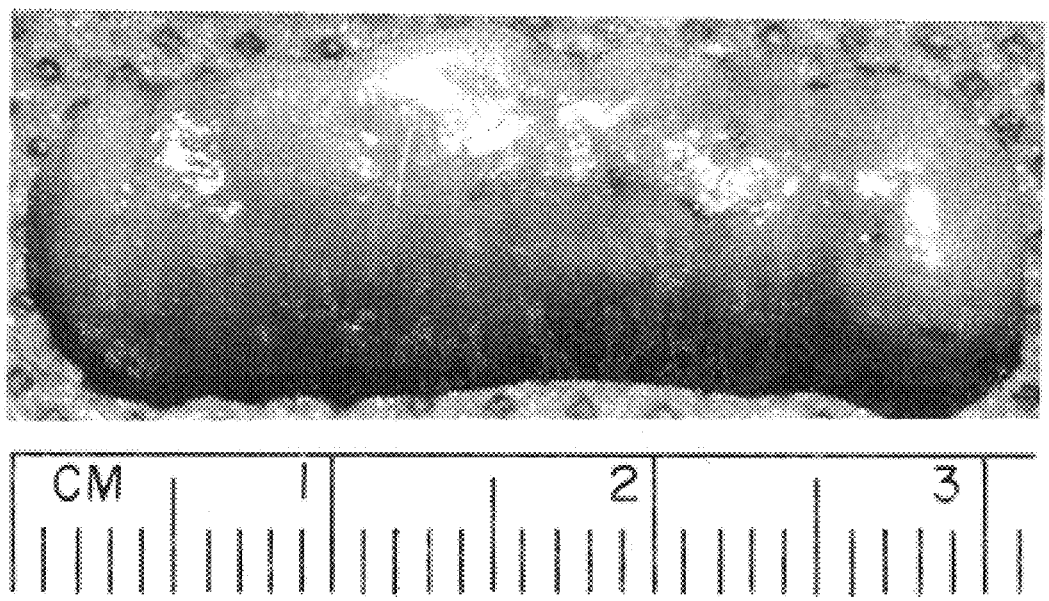
Figure 2C:
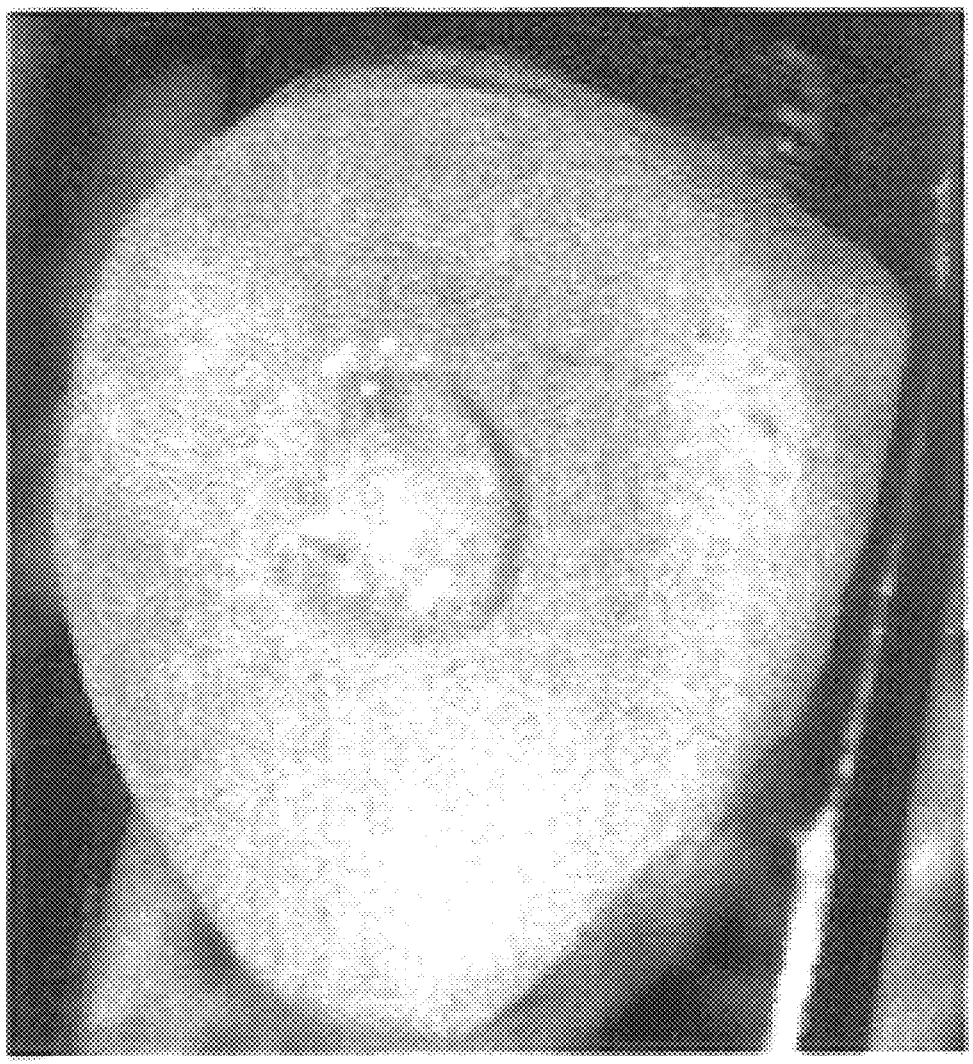

All the animals survived until sacrifice without any noticeable untoward effects. At retrieval, all of the polymer scaffolds seeded with cells formed cartilaginous structures, whereas the control scaffolds failed to form. Gross examination of the retrieved specimens showed the presence of well formed milky-white rod shaped solid cartilage structures which were identical in size (about 1 cm in diameter× about 3 cm in length) to the initial implant (FIG. 2).

Figure 3A:
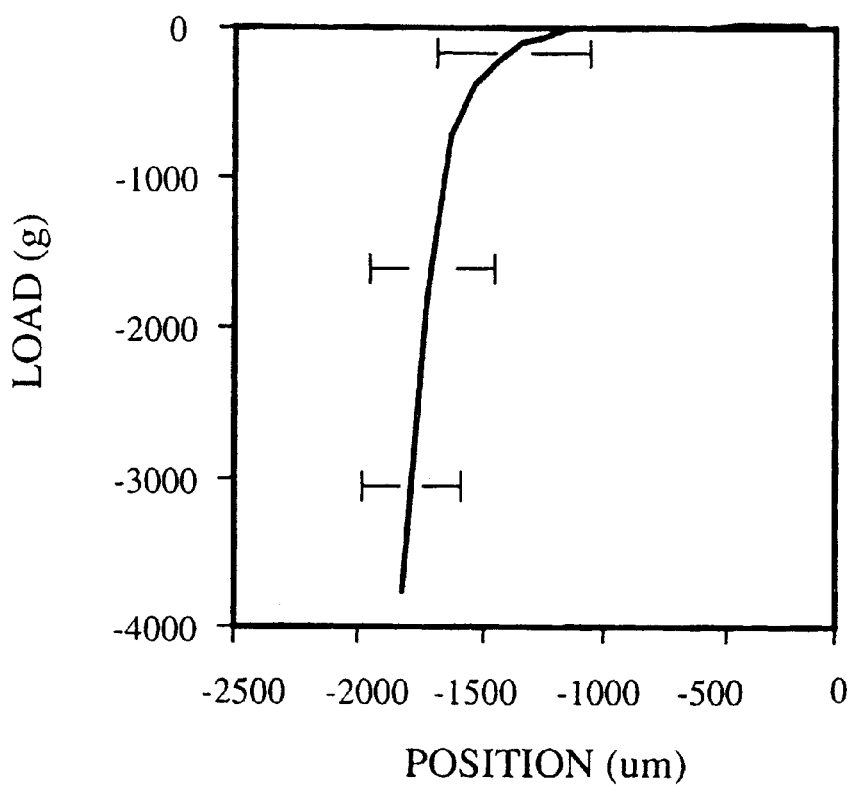
FIG. 3 depicts biomechanical properties of the engineered cartilage rods in (A) compression studies (n=3); (B) tension-relaxation studies (n=3); (C) bending-compression relaxation studies (n=3); and (D) bending-compression relaxation studies performed at a speed of 20,000 μm/sec for 5 consecutive cycles (n=3).
Figure 3B:
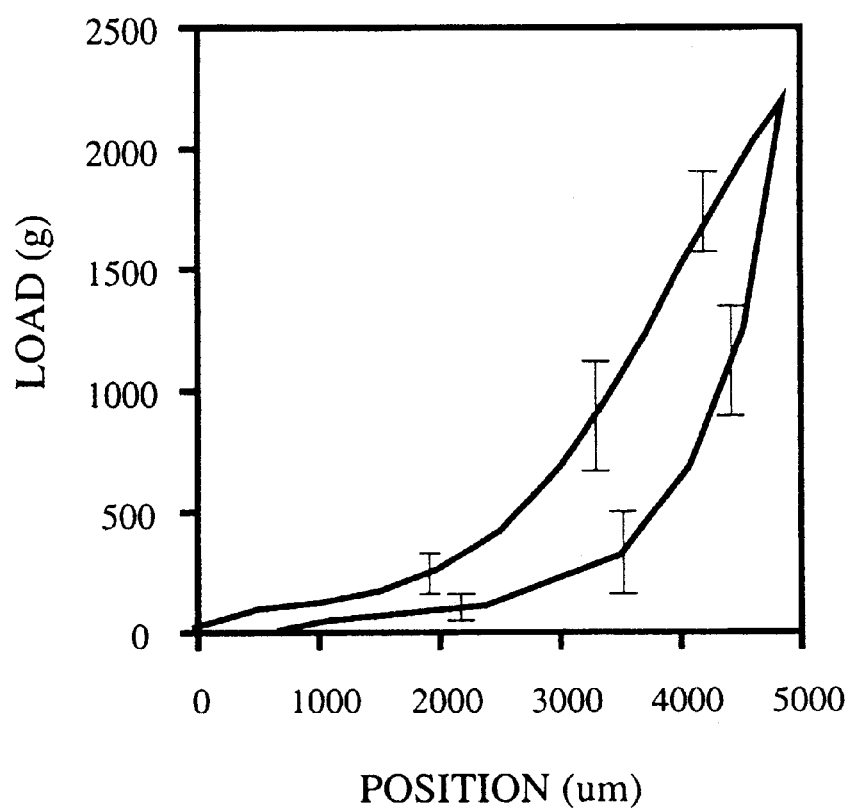
Figure 3C:
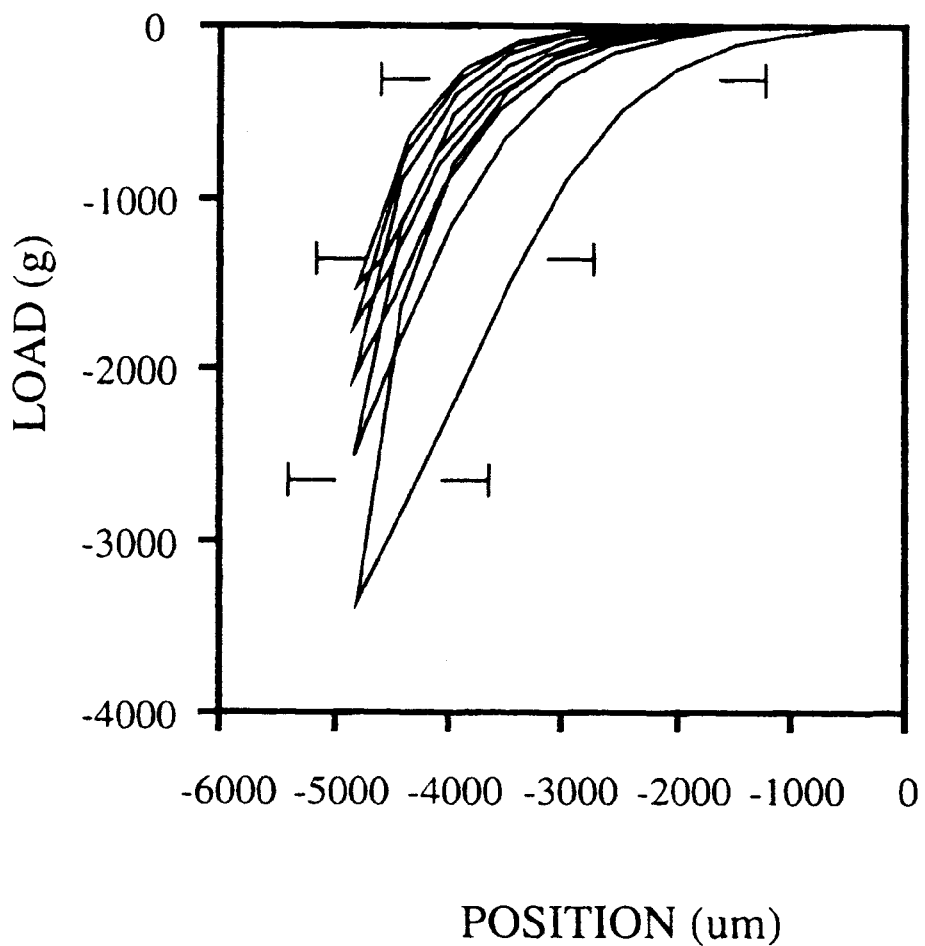
Figure 3D:
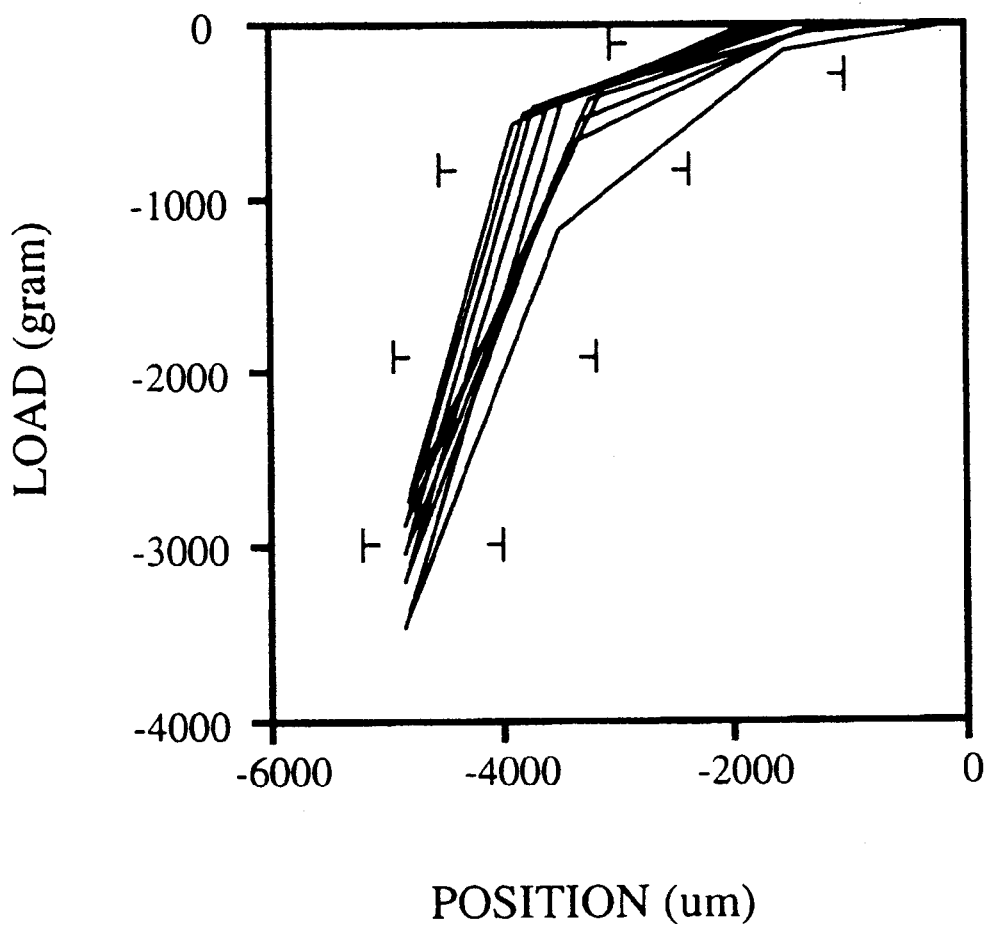

To determine whether the engineered cartilage rods possess the mechanical properties required to maintain penile rigidity, a series of stress relaxation tests were performed. The compression, tension and bending studies showed that the cartilage structures were readily elastic and can withstand high degrees of pressure. The compression studies showed that the retrieved cartilage rods were able to withstand high degrees of pressure (FIG. 3A). A ramp compression speed of about 200 $\mu$m/sec, applied to each cartilage rod up to about 3000 $\mu$m in distance, resulted in about 3.7 kg of resistance. The tension relaxation studies demonstrated that the retrieved cartilage rods were able to withstand stress and were able to return to their initial state while maintaining the biomechanical properties (FIG. 3B). A ramp tension speed of about 200 $\mu$m/second applied to each cartilage created a tensile strength of 2.2 kg, which physically lengthened the rod to about 4800 $\mu$m. Relaxation of tension at the same speed resulted in the retraction of the cartilage rod to the initial state. The bending studies performed at two different speeds showed that the engineered cartilage rods are durable, malleable, and are able to retain their mechanical properties (FIGS. 3C, D). Cyclic compression, performed at rates of about 500 $\mu$m/sec and about 20,000 $\mu$m/sec, demonstrated that the engineered cartilage rods can withstand up to about 3.5 kg of pressure at a predetermined distance of 5000 $\mu$m. The relaxation phase of the cyclic compression studies showed that the engineered cartilage rods were able to maintain their tensile strength. None of the cartilage rods were ruptured during the biomechanical stress relaxation studies.

Figure 4A:
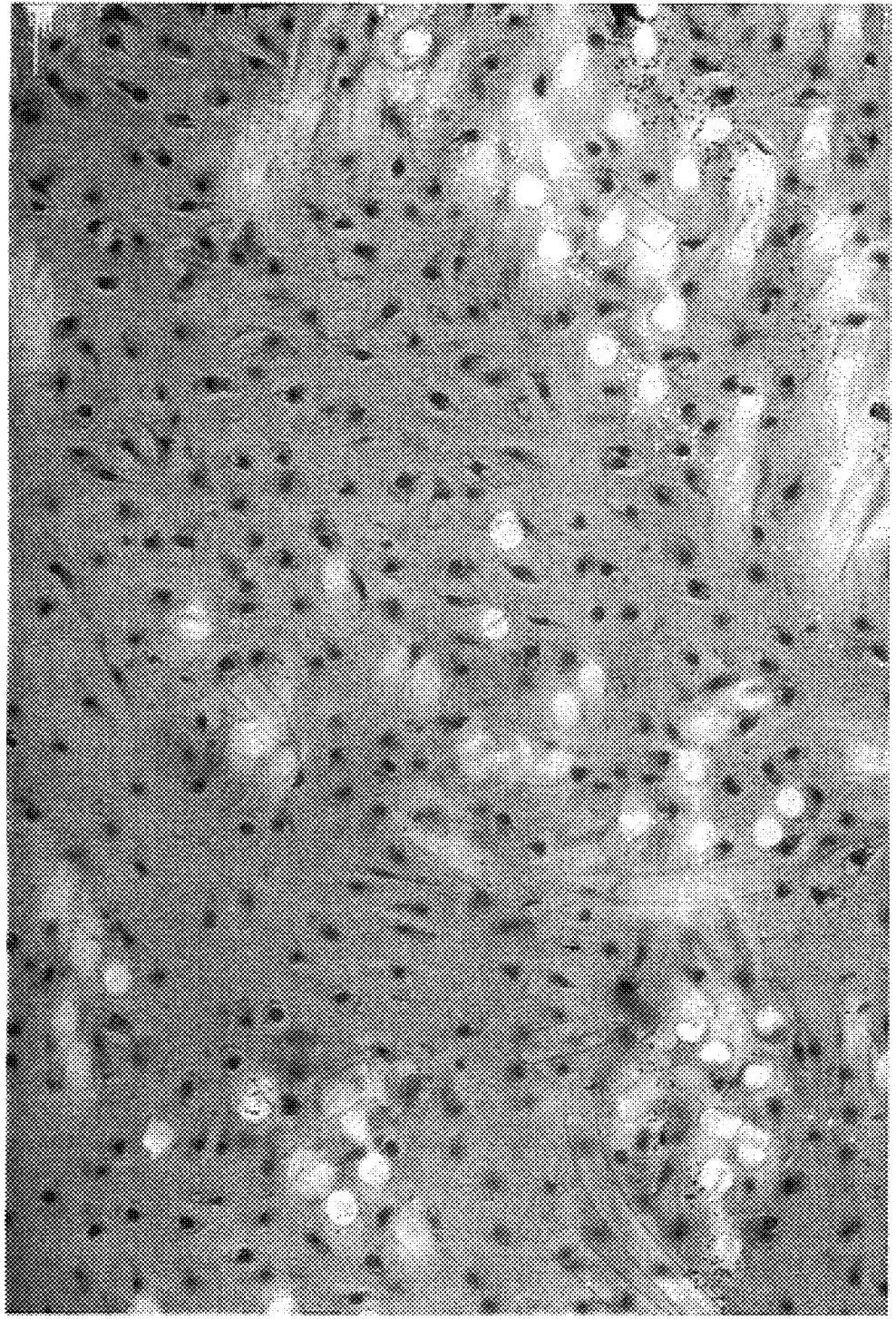
FIG. 4 depicts retrieved cartilage rod specimens at 2 months showing (A) chondrocytes enclosed within lacunae and the presence of undegraded polymer fibers under hematoxylin and eosin. Reduced from ×400) and (B) the presence of highly sulfated mucopolysaccharides under toluidine blue staining.
Figure 4B:
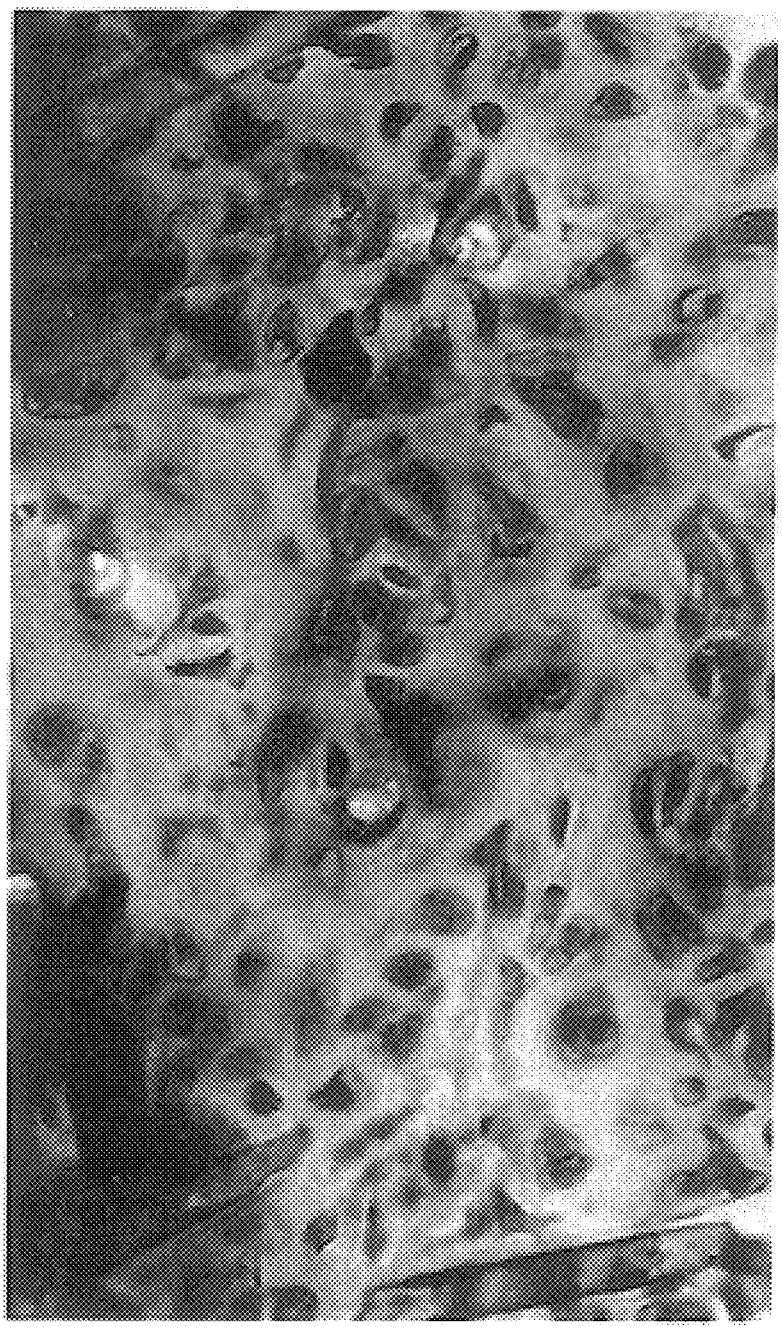
Figure 5A:
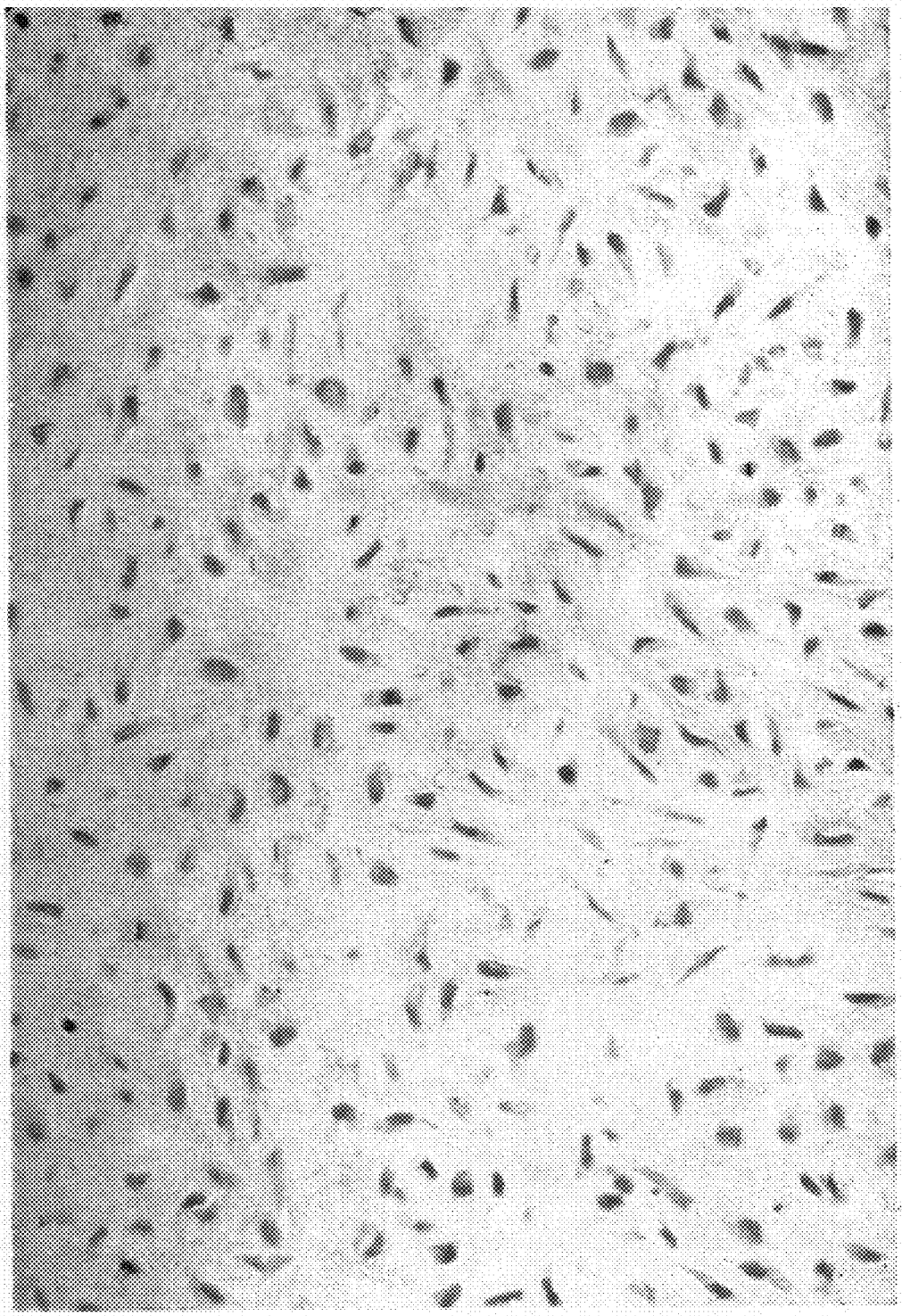
FIG. 5 depicts retrieved cartilage rod specimens at 6 months showing (A) completely degraded polymer fibers replaced by cartilage under hematoxylin and eosin and (B) under aldehyde fuschin-alcian blue staining. (Reduced from ×400).
Figure 5B:
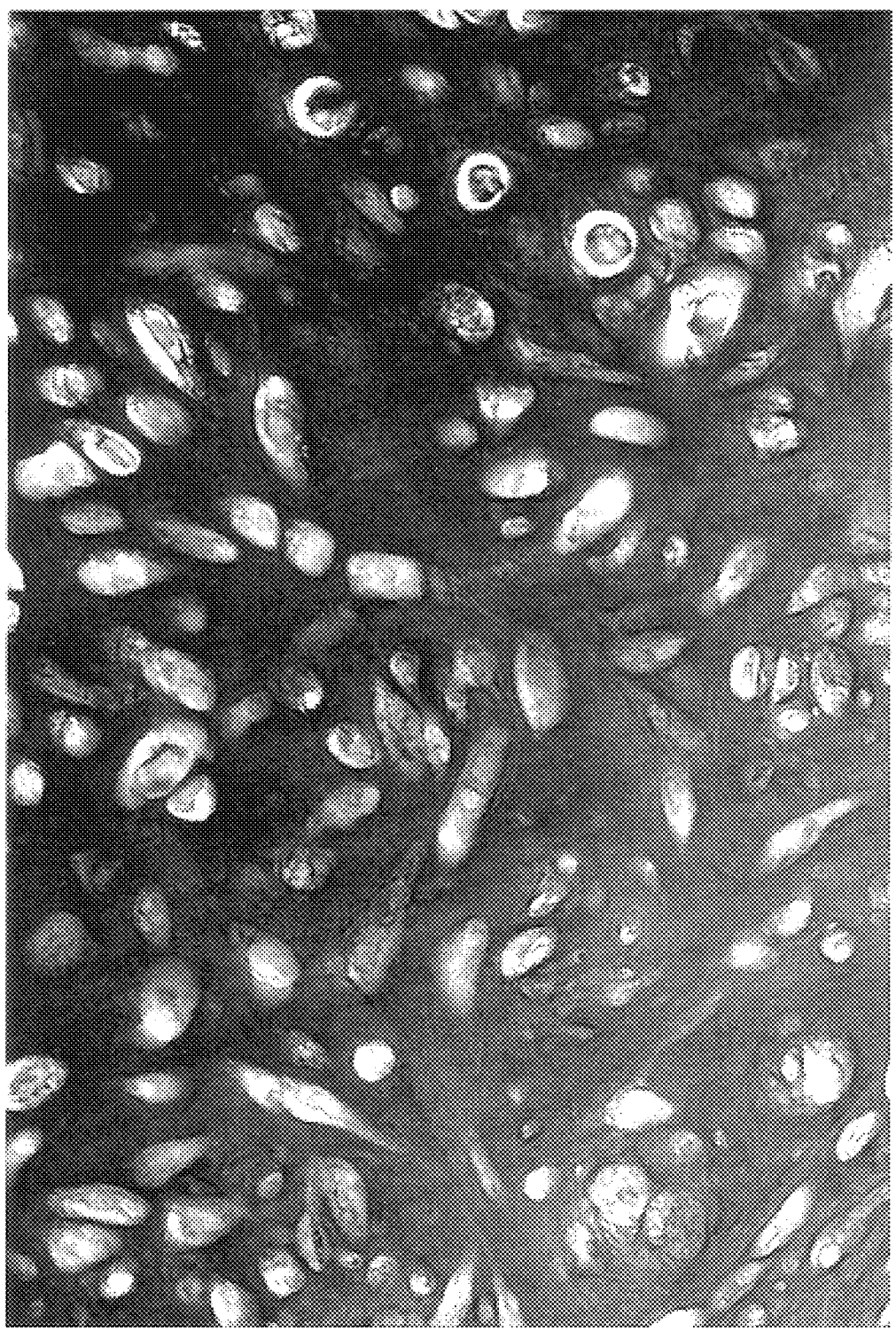

Histochemical analyses with hematoxylin and eosin, aldehyde fuschin alcian blue and toluidine blue staining demonstrated the presence of mature and well formed chondrocytes in all the implants. Histological examination with hematoxylin and eosin showed the presence of mature and well formed cartilage in all the chondrocyte-polymer implants. The polymer fibers were progressively replaced by cartilage with time progression (1, 2, 4 and 6 months). Undegraded polymer fibers were observed at about 1 and about 2 months after implantation (FIG. 4). However, remnants of polymer scaffolds were not present in the cartilage rods at about 6 months (FIG. 5). Aldehyde fuschin-alcian blue and toluidine blue staining demonstrated the presence of highly sulfated mucopolysaccharides which are differentiated products of chondrocytes (FIGS. 4, 5). There was no evidence of cartilage formation in the controls.

Example 4

Cell Culturing and Seeding using Rabbit Chondrocytes.

A schematic outline of this Example is shown in FIG. 6. Autologous chondrocytes harvested from rabbit ear were dissected into small fragments (2×2 mm). Chondrocytes were harvested under sterile conditions using a previously described technique (Atala, A., et al., J Urol, 150: 745–747, 1993; Atala, A., et al., J Urol, 152–641–643, 1994). Briefly, the dissected cartilage fragments were digested in 3% collagenase type II solution (Worthington Biochemical Corp., Lakewood, N.J.) for 6–8 hours. The recovered cells were washed with phosphate buffered saline and were plated in culture dishes. The isolated cells were grown in culture in Hamms F-12 media (Gibco, Grand Island, N.Y.) containing 10% fetal calf serum (Biowhittaker, Walkersville, Md.), 5 $\mu$g/ml ascorbic acid, 100 $\mu$g/ml streptomycin and 100 U/ml penicillin. The cells were incubated at 37°. in the presence of 5% $CO_2$. Chondrocytes were expanded until sufficient cell quantities were available. The cells were trypsinized, collected, washed and counted for seeding. Chondrocytes were seeded onto pre-formed poly-L-lactic acid coated polyglycolic acid polymer rods at a concentration of $50 \times 10^6$ chondrocytes/$Cm^3$. The cell-polymer rods were implanted immediately after seeding.

A total of 18 chondrocyte-polymer scaffolds were implanted in the corporal spaces of 10 rabbits. Bilateral intra corporal implantations of the cell-polymer scaffolds were performed in 8 rabbits, while the remaining 2 animals received unilateral implantation, leaving the other corpus cavemosum intact as controls. Animals were sacrificed at 1 and 2 months (3 each), and at 3 and 6 months (2 each) after implantation. The two control animals were sacrificed at 1 month and 6 months. The implants were retrieved, and analyzed grossly and histologically. Five micron sections of formalin fixed paraffin embedded tissues were cut and stained with hematoxylin and eosin (H&E), aldehyde fuschin-alcian blue and toluidine blue.

All animals tolerated the implants for the duration of the study, without any noticeable complications. Gross examination at retrieval showed the presence of well formed milky white cartilage structures within the corpora after 1 month (FIG. 7). The retrieved cartilage rod structures maintained approximately the same sizes as the initial implants within the corporal bodies. The corpora without implantation showed normal cavernosal tissue. There was no evidence of erosion, inflammation or infection in any of the implanted cartilage rod sites.

Histological analyses with hematoxylin, and eosin showed the presence of mature and well formed cartilage in all the chondrocyte-polymer implants (FIG. 8). The polymer fibers were progressively replaced by cartilage with increasing time (1, 2,4 and 6 months). All polymers were fully degraded by 2 months. Aldehyde fuschin-alcian blue and toluidine blue staining demonstrated the presence of highly sulfated mucopolysaccharides which are differentiated products of chondrocytes (FIG. 9).

All polymers were fully degraded by 2 months. There was no evidence of erosion or infection in any of the implant sites. Histological analyses with alcian blue and toluidine blue staining demonstrated the presence of mature and well formed chondrocytes in the retrieved implants.

Autologous chondrocytes seeded on pre-formed biodegradable polymer structures are able to form cartilage structures within the rabbit corpus cavemosum. Thus, this technology has been shown to be useful for the creation of autologous penile prostheses.

Other embodiments and uses of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

What is claimed is:

1. An implantable structural member for use in treating a patient having an anatomical defect not caused by absent, damaged, or diseased cartilage and which can be treated, at least in part, by providing structural support to adjacent tissue; said structural member comprising a polymeric matrix shaped in the form of the desired support member and having dissociated cartilage-forming cells deposited on and in said matrix whereby upon implantation a cartilaginous structural member is formed having controlled biomechanical properties and a tensile strength of at least about 2.2 kg, providing the required structural support in the area of said defect.

2. The structural member of claim 1 wherein the polymeric matrix comprises a biocompatible material selected from the group consisting of cellulose ether, cellulose, cellulosic ester, fluorinated polyethylene, phenolic, poly-4-rethylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends thereof.

3. The structural member of claim 1 wherein the polymeric matrix comprises a biodegradable material.

4. The structural member of claim 3 wherein the biodegradable material is selected from the group consisting of a polyglycolic acid polymer, a polyglactin polymer, and mixtures and composites thereof.

5. The structural member of claim 3 which is strengthened by coating at least part of some structural member with a liquefied polymer.

6. The structural member of claim 5 wherein said liquefied polymer is a copolymer of 50:50 poly-DL-lactide-co-glycolide.

7. The -structural member of claim 1 wherein said cartilage-forming cells are chondrocytes.

8. The structural member of claim 1 wherein said support member is an elongated cylinder further comprising means adapted to receive a urethra.

9. The structural member of claim 7 wherein said means adapted to receive a urethra is a longitudinal groove along its length.

10. The structural member of claim 1 where in said support member is a hollow cylindrical tube with a wall thickness and a bore along its length.

11. The structural member of claim 10 wherein the hollow cylindrical tube is adapted to receive a urethra.

12. The structural member of claim 10 wherein the wall thickness is variable longitudinally.

13. The structural member of claim 1 wherein said cylinder has a variable structural strength along its longitudinally length.

14. The structural member of claim 1 further comprising anchoring means on one end for the attachment of said implant to the descending pelvis.

15. The structural member of claim 1 which has a tensile strength of at least about 3.7 kg.

16. The structural member of claim 1 which can withstand cyclic compression performed at rates of from 500 $\mu$m per second to 20,000 $\mu$m per second.

17. A method for reconstructing the penis of a patient in need of such treatment comprises the steps of
   (a) providing a biocompatible synthetic or natural polymeric matrix shaped to form a structural member adopted to fit within the corpora cavernosa of said penis;
   (b) depositing cartilage-forming cells on and in said matrix to form a matrix/cell construct and
   (c) implanting said material construct into the corpora cavernosa of said patient, whereby a cartilaginous structural member is formed in vivo having controlled biomechanical properties providing the reconstructed penis with sufficient stiffness and bending strength to serve as a functional organ.

18. The method of claim 17 wherein the polymeric matrix comprises a biocompatible material selected from the group consisting of cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends thereof.

19. The method of claim 17 wherein the polymeric matrix comprises a biodegradable material.

20. The method of claim 19 wherein the biodegradable material is selected from the group consisting of a polyglycolic acid polymer, a polyglactin polymer, and mixtures and composites thereof.

21. The method of claim 17 wherein said cartilage-forming cells are chondrocytes.

22. The method of claim 17 wherein said support member is an elongated cylinder further comprising means adapted to receive a urethra.

23. The method of claim 22 wherein said means adapted to receive a urethra is a longitudinal groove along its length.

24. The method of claim 17 where in said support member is a hollow cylindrical tube with a wall thickness and a bore along its length.

25. The method of claim 24 wherein the hollow cylindrical tube is adapted to receive a urethra.

26. The method of claim 24 wherein the wall thickness is variable longitudinally.

27. The method of claim 17 wherein said cylinder has a variable structural strength along its longitudinally length.

28. The method of claim 17 further comprising anchoring means on one end for the attachment of said implant to the descending pelvis.

29. The method of claim 17 which has a tensile strength of at least about 2.2 kg.

30. The method of claim 17 which has a tensile strength of at least about 3.7 kg.

31. The method of claim 17 which can withstand cyclic compression performed at rates of from 500 $\mu$m per second to 20,000 $\mu$m per second.

* * * * *